(12) United States Patent
Roy et al.

(10) Patent No.: US 11,399,945 B2
(45) Date of Patent: Aug. 2, 2022

(54) CEMENTED ACETABULAR CONSTRUCT WITH LOCKED MODULAR SLEEVE

(71) Applicant: Howmedica Osteonics Corp., Mahwah, NJ (US)

(72) Inventors: Shammodip Roy, Mahwah, NJ (US); Arlen Dale Hanssen, Rochester, MN (US); Matthew P. Abdel, Rochester, MN (US); Mark W. Pagnano, Chatfield, MN (US)

(73) Assignee: Howmedica Osteonics Corp., Mahwah, NJ (US)

( * ) Notice: Subject to any disclaimer, the term of this patent is extended or adjusted under 35 U.S.C. 154(b) by 218 days.

(21) Appl. No.: 16/750,550

(22) Filed: Jan. 23, 2020

(65) Prior Publication Data
US 2020/0237517 A1    Jul. 30, 2020

Related U.S. Application Data

(60) Provisional application No. 62/796,784, filed on Jan. 25, 2019.

(51) Int. Cl.
*A61F 2/34* (2006.01)
*A61F 2/30* (2006.01)

(52) U.S. Cl.
CPC ...... *A61F 2/34* (2013.01); *A61F 2002/30003* (2013.01); *A61F 2002/30474* (2013.01); *A61F 2002/30919* (2013.01); *A61F 2002/3483* (2013.01)

(58) Field of Classification Search
CPC .. A61F 2/32; A61F 2/34; A61F 2/4603; A61F 2002/30474; A61F 2002/30919; A61F 2002/4631; A61F 2002/3429; A61F 2002/3435
See application file for complete search history.

(56) References Cited

U.S. PATENT DOCUMENTS

| | | | |
|---|---|---|---|
| 3,829,904 | A | 8/1974 | Ling et al. |
| 3,894,297 | A | 7/1975 | Mittelmeier et al. |
| 4,141,088 | A | 2/1979 | Treace et al. |
| 4,172,296 | A | 10/1979 | D'Errico |
| 4,437,193 | A | 3/1984 | Oh |
| 4,619,658 | A | 10/1986 | Pappas et al. |

(Continued)

OTHER PUBLICATIONS

Stryker Orthopedics, Trident Constrained Acetabular Insert, Surgical Protocol, entire document (Year: 2012).*

(Continued)

*Primary Examiner* — Brian A Dukert
(74) *Attorney, Agent, or Firm* — Lerner, David, Littenberg, Krumholz & Mentlik, LLP (57) ABSTRACT

In one embodiment, the present disclosure relates to an acetabular implant system with a liner and a sleeve. The liner includes a convex outer surface shaped to correspond to an interior of an acetabular cup and has an equatorial region and a polar region. The convex outer surface includes a plurality of liner engagement features thereon. The sleeve includes an inner surface with a plurality of sleeve engagement features thereon. The inner surface of the sleeve is sized to be flush with the convex outer surface of the liner. When the sleeve is engaged with the liner, the liner engagement features engage the sleeve engagement features.

20 Claims, 8 Drawing Sheets

(56) References Cited

U.S. PATENT DOCUMENTS

| | | | |
|---|---|---|---|
| 4,623,352 A * | 11/1986 | Oh | A61F 2/34 623/22.28 |
| 4,642,123 A | 2/1987 | Noiles | |
| 4,695,282 A | 9/1987 | Forte et al. | |
| 4,718,911 A | 1/1988 | Kenna | |
| 4,795,470 A | 1/1989 | Goymann et al. | |
| 4,822,369 A | 4/1989 | Oueveau et al. | |
| 4,883,490 A | 11/1989 | Oh | |
| 4,961,748 A | 10/1990 | Frey et al. | |
| 5,019,105 A | 5/1991 | Wiley | |
| 5,092,897 A | 3/1992 | Forte | |
| 5,549,701 A | 8/1996 | Mikhail | |
| 5,766,260 A | 6/1998 | Whiteside | |
| 5,824,108 A | 10/1998 | Huebner | |
| 6,610,097 B2 * | 8/2003 | Serbousek | A61F 2/34 623/22.24 |
| 6,758,864 B2 | 7/2004 | Storer et al. | |
| 6,811,569 B1 | 11/2004 | Afriat et al. | |
| 7,918,895 B2 | 4/2011 | Isch et al. | |
| 8,128,631 B2 | 3/2012 | Johnson et al. | |
| 8,226,728 B2 | 7/2012 | Preuss et al. | |
| 8,308,811 B2 | 11/2012 | Newsome et al. | |
| 8,679,187 B2 | 3/2014 | Allen et al. | |
| 8,753,404 B2 | 6/2014 | Lambert et al. | |
| 2001/0037156 A1 | 11/2001 | Burstein et al. | |
| 2002/0068980 A1 | 6/2002 | Serbousek et al. | |
| 2005/0080490 A1 | 4/2005 | Bertram | |
| 2007/0118227 A1 | 5/2007 | King et al. | |
| 2008/0294266 A1 | 11/2008 | Steinberg | |
| 2009/0088864 A1 | 4/2009 | Lewis et al. | |
| 2012/0143344 A1 | 6/2012 | Shea et al. | |
| 2014/0303743 A1 | 10/2014 | Choudhury et al. | |
| 2015/0025647 A1 | 1/2015 | Zhang | |
| 2017/0181857 A1 | 6/2017 | Wang et al. | |

OTHER PUBLICATIONS

Extended European Search Report for Application No. EP20153178.7, dated May 26, 2020, pp. 1-3.

* cited by examiner

CEMENTED ACETABULAR CONSTRUCT WITH LOCKED MODULAR SLEEVE

CROSS REFERENCE TO RELATED APPLICATION

This application claims the benefit of the filing date of U.S. Provisional Patent Application No. 62/796,784, filed Jan. 25, 2019, the disclosure of which is hereby incorporated by reference herein in its entirety.

BACKGROUND OF THE INVENTION

In many instances following an initial surgery to repair a joint, a revision surgery is required, which generally involves implantation of new prostheses. Revision surgery may be required due to underlying maladies such as infection or dislocation, or simply because of the wear of the initially implanted prostheses.

When revision surgery involves reconstruction of the hip joint, and the reconstruction only requires the removal of an inner acetabular liner and not an outer shell secured to the acetabulum, such as circumstances where the implants are part of a modular dual mobility system, such a task is often very difficult and time consuming to perform intra-operatively. Indeed, it is a labor intensive and potentially damaging exercise. For example, in an intra-operative setting, conventional tools such as osteotomes or drills are often used to chip away exposed cement mantle between an outer acetabular shell and an inner liner to remove the liner. This process is time consuming and may result in damage to the acetabular shell and/or the bone underneath it. In other types of implant configurations where the acetabular shell is press-fit to the acetabulum without screws, an acetabular extraction device may be used to remove the acetabular shell, cement mantle and the inner liner. In the latter circumstance, the significant forces applied to the cement mantle between the acetabular elements as part of the process may still pose a high risk of damage to bone or even bone loss may occur during the extraction process. This is particularly so as the cement must be removed one small fragment at a time. Moreover, due to the hemispherical geometry of the cement mantle in between the acetabular shell and the inner liner, it is difficult to access the cement toward the polar regions of the acetabular elements with conventional tools.

Thus, a need exists for improved devices, systems and methods relating to hip implants that are also adapted for revision surgery.

BRIEF SUMMARY OF THE INVENTION

In one aspect, the present disclosure relates to an assembly with an inner hemispherical construct, also referred to as an acetabular liner, and a sleeve mechanically fixed to a surface of the inner hemispherical construct. In use, the assembly is fitted into an outer acetabular construct such as an acetabular shell in a mammalian body and secured thereto with cement.

In some embodiments, the sleeve is a partial hollow hemisphere with an inner surfaces having protrusions thereon. The protrusions may include two separate sets, each at a different depth of the sleeve and spaced equally from one another within one set but out of phase with each other between sets. The sleeve is sized to fit over the liner in a flush manner and is further arranged to lock to the liner via the protrusions. In particular, the liner includes a plurality of perimeter grooves extending circumferentially around the liner and a plurality of polar grooves extending between equatorial and polar regions of the liner. The sleeve is locked to the liner through a snap fit between each protrusion and one of the perimeter grooves.

In some embodiments where the assembly is fitted into an outer hemispherical construct, the sleeve is made of a polymer while the inner hemispherical construct and the outer hemispherical construct are metallic. In this manner, the structure of the assembly is such that when the assembly is in place within an outer hemispherical construct, the polymer sleeve insulates cement between the metallic outer hemispherical construct and the metallic inner hemispherical construct so that the cement is only exposed to metal on one side in the equatorial region.

In one embodiment, the present disclosure relates to an acetabular implant system that includes an acetabular cup, a liner and a sleeve. The liner includes a convex outer surface shaped to correspond to the acetabular cup and has an equatorial region and a polar region. The convex outer surface of the liner includes a plurality of liner engagement features thereon. The sleeve includes an inner surface with a plurality of sleeve engagement features thereon and is sized to be flush with the convex outer surface of the liner. When the sleeve is engaged with the liner, the liner engagement features engage the sleeve engagement features.

In some embodiments, when the sleeve is engaged with the liner, the sleeve may cover a first portion of the polar region of the convex outer surface of the liner without covering a second portion of the polar region. In other embodiments, the plurality of liner engagement features may include a circumferentially extending recess parallel to a rim of the liner. In still further embodiments, the plurality of sleeve engagement features may be protrusions shaped to fit within the circumferentially extending recess on the convex outer surface of the liner. In still further embodiments, the plurality of liner engagement features may include a second circumferentially extending recess parallel to the rim of the liner. Additionally, the protrusions on the inner surface of the sleeve may include a first protrusion at a first distance from a rim of the sleeve and a second protrusion at a second distance from the rim of the sleeve. The protrusions may be positioned such that the first protrusion fits within the circumferentially extending recess and the second protrusion fits within the second circumferentially extending recess. In some embodiments, the sleeve may include an outer surface with a second plurality of sleeve engagement features thereon. In some embodiments, the plurality of liner engagement features may include a plurality of recesses extending from a pole of the liner to a rim of the liner. Similarly, the second plurality of sleeve engagement features may include a plurality of recesses aligned with the plurality of recesses on the convex outer surface of the liner when the sleeve is engaged with the liner. In other embodiments, the plurality of liner engagement features may be one of recesses and protrusions and the plurality of sleeve engagement features may be the other of recesses and protrusions. In some embodiments, the sleeve may be a polymeric material and the liner may be a metallic material.

In one embodiment of the disclosure, an acetabular implant includes an acetabular cup, a liner and a sleeve. The acetabular cup is adapted to seat within an acetabulum of a mammal, the liner is disposed in the acetabular cup, and the sleeve is engaged to a portion of an outer surface of the liner such that the sleeve is disposed in between the acetabular cup and the liner. With the sleeve engaged to the liner, the liner is cemented to the acetabular cup.

In some embodiments, the sleeve may be a segment of a hollow sphere between two parallel planes where one of the two parallel planes bisects the hollow sphere. In some embodiments, the liner may include an equatorial region and a polar region such that the sleeve separates the liner from the acetabular cup solely in the equatorial region. In some embodiments, the cement for engagement of the liner with the sleeve is disposed between the liner and the acetabular cup over an entirety of both the equatorial region and the polar region of the liner. In some embodiments, the sleeve may include an inner surface with protrusions thereon. The protrusions may be engaged to corresponding recesses on an outer surface of the liner. In some embodiments, the recesses on the outer surface of the liner may extend circumferentially and in parallel to a rim of the liner.

In another aspect, the present disclosure relates to an acetabular implant system with a liner and a sleeve. In one embodiment, the liner includes a convex outer surface shaped to correspond to an interior of an acetabular cup and has an equatorial region and a polar region. The convex outer surface of the liner includes a plurality of liner engagement features thereon. The sleeve includes an inner surface with a plurality of sleeve engagement features thereon and is sized to be flush with the convex outer surface of the liner. When the sleeve is engaged with the liner, the liner engagement features engage the sleeve engagement features.

In some embodiments, when the sleeve is engaged with the liner, the sleeve may cover a first portion of the polar region of the convex outer surface of the liner without covering a second portion of the polar region. In other embodiments, the plurality of liner engagement features may include a circumferentially extending recess parallel to a rim of the liner. In still further embodiments, the plurality of sleeve engagement features may be protrusions shaped to fit within the circumferentially extending recess on the convex outer surface of the liner. In still further embodiments, the plurality of liner engagement features may include a second circumferentially extending recess parallel to the rim of the liner. Additionally, the protrusions on the inner surface of the sleeve may include a first protrusion at a first distance from a rim of the sleeve and a second protrusion at a second distance from the rim of the sleeve. The protrusions may be positioned such that the first protrusion fits within the circumferentially extending recess and the second protrusion fits within the second circumferentially extending recess.

In some embodiments, the sleeve may include an outer surface with a second plurality of sleeve engagement features thereon. In some embodiments, the plurality of liner engagement features may include a plurality of recesses extending from a location proximal to a pole of the liner to a rim of the liner. Similarly, the second plurality of sleeve engagement features may include a plurality of recesses aligned with the plurality of recesses on the convex outer surface of the liner when the sleeve is engaged with the liner. In other embodiments, the plurality of liner engagement features may be one of recesses and protrusions and the plurality of sleeve engagement features may be the other of recesses and protrusions. In some embodiments, the sleeve may be a polymeric material and the liner may be a metallic material. In some embodiments, the system may include the acetabular cup.

In another aspect, the present disclosure relates to a method of removal of an assembly from within an existing outer acetabular construct of a hip implant. In some embodiments, a conventional tool is used to remove the sleeve of the assembly from the inner acetabular construct of the assembly so that a void is created between the outer construct and the inner construct in the equatorial region. In particular, the tool may be used to cut or chisel the sleeve and adjacent cement, and also to pull the protrusions of the sleeve from the grooves in the inner acetabular construct. Through the void created, the tool may be inserted deep toward a polar region of the inner acetabular construct to pry it out from the remaining cement engagement between the inner acetabular construct and the outer acetabular construct in the polar region.

In one embodiment, the present disclosure relates to a method of removing a liner from an acetabular cup secured to an acetabulum. The method of removal includes the following steps: ensuring that the acetabular cup with the liner cemented therein is accessible to an extent sufficient to remove the liner; causing a sleeve engaged to an outer surface of the liner to become disengaged from the liner; removing the sleeve such that the liner remains at least partially cemented to the acetabular cup in a polar region of the liner; and after removing the sleeve, removing the liner from the acetabular cup such that the acetabular cup remains secured to the acetabulum.

In some embodiments, removing the sleeve may include removing a portion of the cement immediately in between the sleeve and the acetabular cup. In some embodiments, removing the sleeve may leave no more than 60% of an outer surface of the liner covered by cement that secures the liner to the acetabular cup. In some embodiments, causing the sleeve to become disengaged from the liner may include prying a tab on an inside surface of the sleeve from a groove on an outside surface of the liner. In some embodiments, removing the liner may involve rotating the liner relative to the acetabular cup.

BRIEF DESCRIPTION OF THE DRAWINGS

The present disclosure will be better understood on reading the following detailed description of non-limiting embodiments thereof, and on examining the accompanying drawings, in which.

DETAILED DESCRIPTION

The present disclosure relates to devices, assemblies, systems, kits and methods directed to implants used in mammalian joints, such as acetabular implants. Throughout the disclosure, reference is made to an outer acetabular construct, a specific variant of which is an acetabular shell, and an inner acetabular construct, a specific variant of which is an acetabular liner. Each of the outer and inner acetabular constructs are typically of a hollow hemispherical shape and are adapted for securement to each other while the outer acetabular construct is adapted for engagement to a prepared acetabular bone structure in the pelvis. This combination of outer and inner constructs is commonly used as part of a modular dual mobility acetabular implant system.

Generally, the present disclosure relates to a sleeve element adapted to be fixed to an inner acetabular construct, such as a liner, and how the combination of the sleeve and the inner acetabular construct improve an overall implant system when combined with an outer acetabular construct, such as an acetabular shell. In particular, the inclusion of the sleeve locked to an outer surface of the inner acetabular construct improves the relationship between the inner and outer acetabular constructs over a life cycle of their use when compared to the relationship of the inner and outer acetabular constructs without the sleeve.

Figure 1:
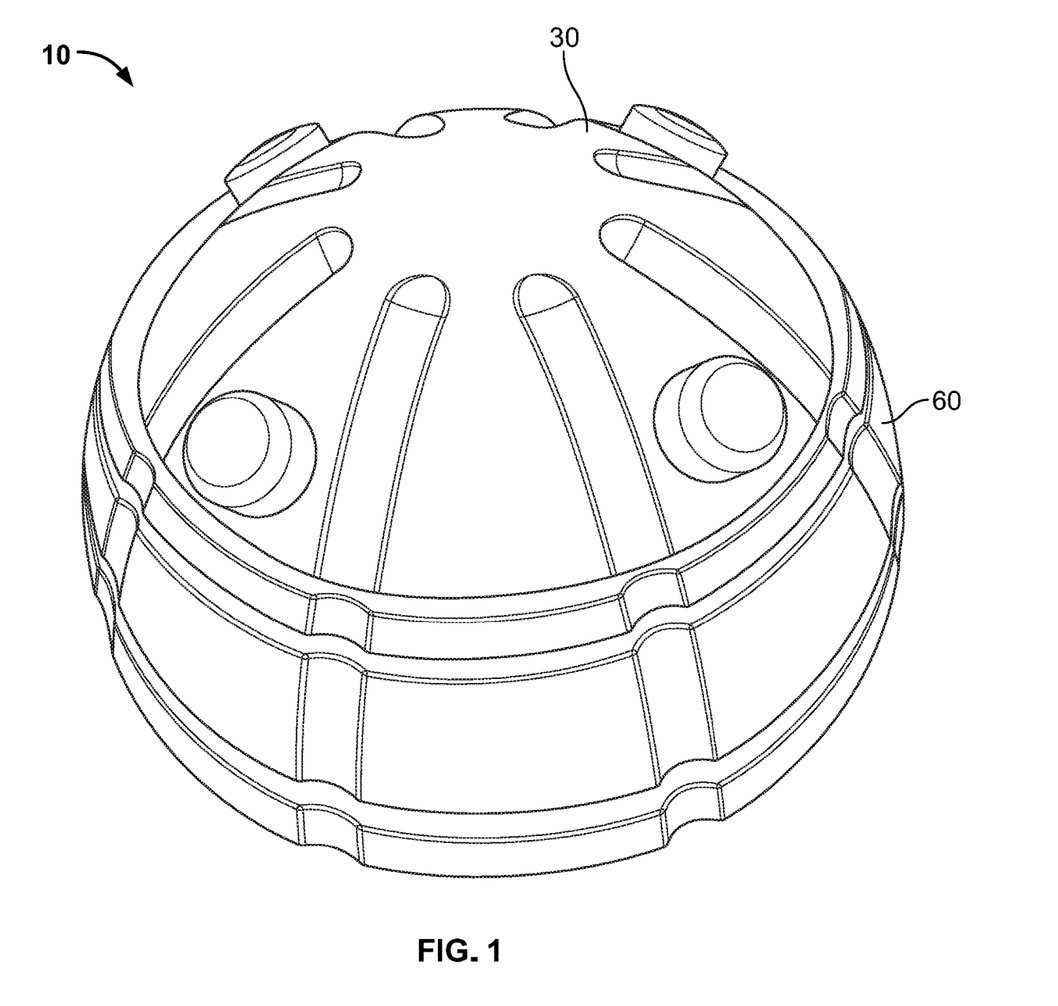
FIG. 1 is a perspective view of an acetabular assembly according to one embodiment of the disclosure.
Figure 2A:
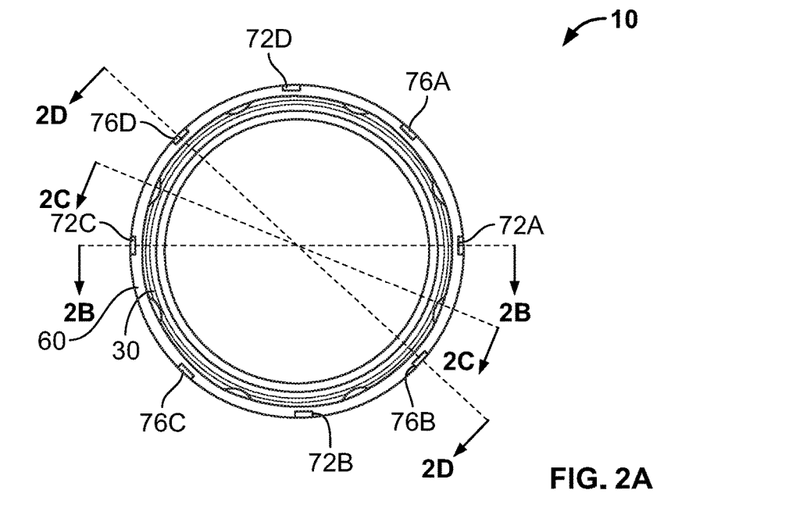
FIG. 2A is a partial top view of a liner of the assembly shown in FIG. 1.
Figure 2B:
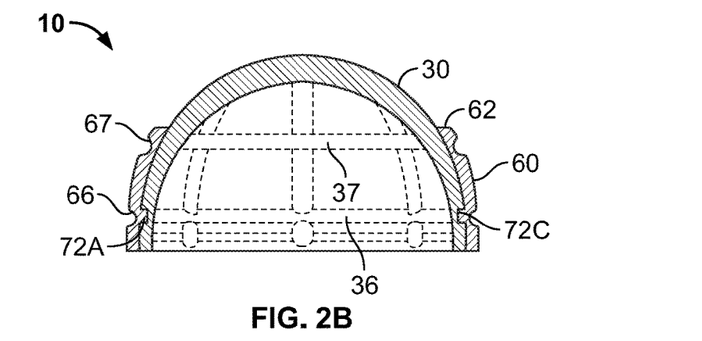
FIGS. 2B-2D are cross-sectional views of the assembly shown in FIG. 1.
Figure 2C:
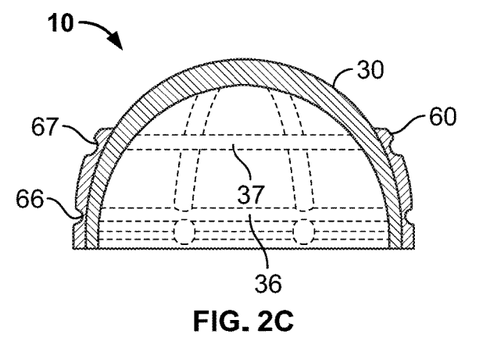
Figure 2D:
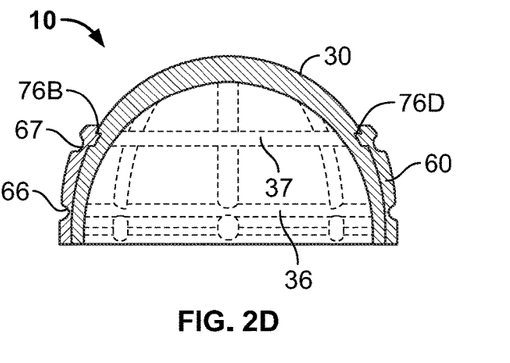

In one aspect, the present disclosure relates to an acetabular assembly that includes an inner acetabular construct, such as a liner, and a sleeve. Although the inner acetabular construct is referred to as a liner in many embodiments of the disclosure, it should be appreciated that the inner acetabular construct is not limited to a liner and may be another similar structure. One embodiment of an acetabular assembly 10 with liner 30 and sleeve 60 is shown in FIG. 1. Sleeve 60 is sized and includes engagement features so that it is mechanically fixed to an outer surface of liner 30 when it is pressed thereon. A combined structure of sleeve 60 and liner 30 defines assembly 10. Various sectional views of assembly 10 with sleeve 60 locked to liner 30 are shown in FIGS. 2B-2D, with references to a location of each sectional view identified in FIG. 2A.

Figures 3, 4, 5, 6:
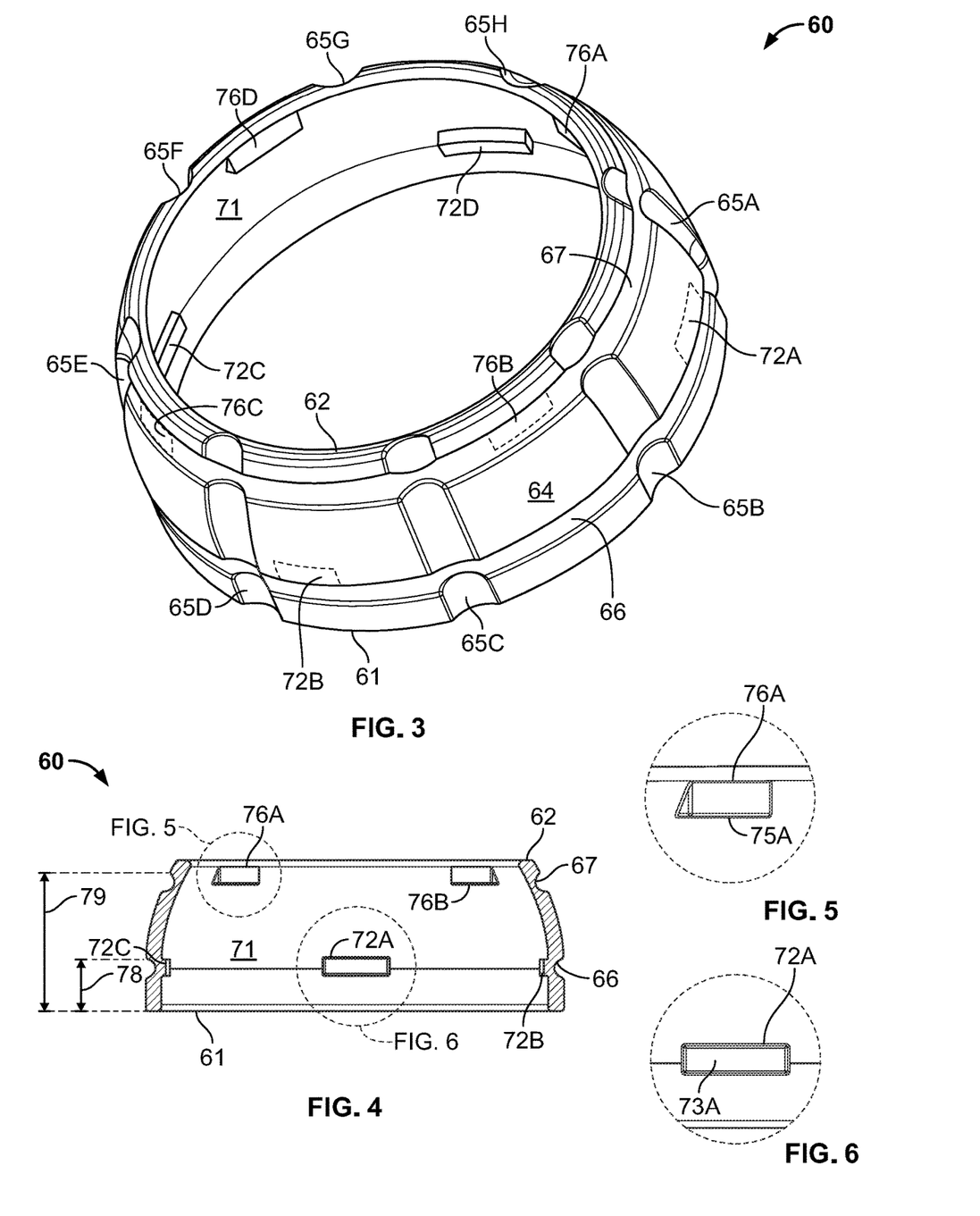
FIG. 3 is a perspective view of a sleeve of the assembly shown in FIG. 1.
FIG. 4 is a cross-sectional view of the sleeve shown in FIG. 3.
FIGS. 5 and 6 are close up partial cross-sectional views of the sleeve shown in FIG. 3.

Turning to the individual components of assembly 10, sleeve 60 is shown in FIG. 3. The sleeve is constructed of a conventional polymeric material, though it is contemplated that the sleeve may be formed from other materials or that the material used may incorporate antibiotics. Sleeve 60 is a partial hollow hemisphere without a polar region and resembles a ring. An upper edge 61 of sleeve 60, also referred to as a rim, is close to a maximum circumference of the hemisphere (equivalent to an equator of a sphere), while a lower edge 62 of sleeve 60, parallel to upper edge 61, cuts the hemisphere below what would otherwise be the polar region. In some variants, the upper edge bisects an imaginary spherical shape based on the dimensions of the sleeve. Sleeve 60 includes an outer surface 64 and an inner surface 71, which are convex and concave, respectively. It should be appreciated that although sleeve 60 is shaped to engage with a hemispherical liner or other hemispherical shaped inner acetabular construct, the concepts outlined herein may be adapted or otherwise modified for inner acetabular constructs that are not precisely hemispherical. For example, the sleeve may be shaped to engage a partial spheroid, hemispheroid, or ovoid inner acetabular construct.

Outer surface 64 of sleeve 60 includes a plurality of grooves thereon. It should be appreciated that in alternatives, other forms of engagement features may also be used in place of grooves. Extending around a circumference of sleeve 60 are upper perimeter groove 66 and lower perimeter groove 67. These grooves are recessed relative to outer surface 64 of sleeve. Similarly, other grooves for the sleeve and the liner described throughout the disclosure are recessed relative to respective outer surfaces of such elements. FIG. 3 illustrates that upper perimeter groove 66 is closest to an equatorial region of the sleeve shape while lower perimeter groove 67 is remote from the equatorial region relative to upper perimeter groove 66. Each groove 66, 67 is defined by a rounded trough so that its side edges are at an angle relative to outer surface 64, while across the groove between the sides, the grooves are generally curved. Grooves 66, 67 are parallel to upper edge 61.

Oriented orthogonally to perimeter grooves 66, 67 are polar grooves 65A-65H, spaced at approximately equal intervals around a perimeter of sleeve 60. In FIG. 3, there are eight polar grooves in total. Each polar groove is of a finite length that extends between lower edge 62 and upper edge 61 at the equatorial region. Polar grooves 65A-H as shown are slightly shallower within outer surface 64 than perimeter grooves 66, 67, though the relative depth between the polar grooves and the perimeter grooves may vary from that shown in FIG. 3 and may depend upon the structure of the liner or other inner structure of the construct. Further, a sectional shape of polar grooves 65A-H is a rounded trough with angled interfaces with the outer surface at each side, similar to the perimeter grooves. As noted above with respect to the relative depth of the grooves, a specific geometry of the groove shape for either the perimeter or polar grooves may also vary. Some examples of possible variations are provided below.

Each of grooves 65A-H, 66, 67 is patterned in a manner similar to the grooves on the liner, described in greater detail below. The grooves are shaped and positioned so that the sleeve exhibits performance similar to the liner when in receipt of cement thereon. In particular, the grooves on the sleeve enhance engagement with cement in a manner similar to that achieved with the grooves on the liner.

Inner surface 71 of sleeve 60 includes a plurality of sleeve engagement features in the form of protrusions thereon. Although described here in the context of protrusions, it is contemplated that other forms of engagement features may also be included on the sleeve. As shown in FIG. 3, and also in part in FIGS. 2B-2D, inner surface 71 includes four upper protrusions 72A-D and four lower protrusions 76A-D. When the sleeve is disposed in an acetabulum, the upper protrusions are positioned laterally while the lower protrusions are positioned medially. Protrusions 72A-D, 76A-D may also be described as tabs, though it should be appreciated that the protrusions may vary from a traditional tab shape.

Each upper protrusion 72A-D is located at a first distance from upper edge 61 of sleeve 60. Similarly, as shown in FIG. 4, upper perimeter groove 66 is located at approximately the first distance from upper edge 61. In this manner, a location relative to the upper edge is approximately the same for both upper protrusions 72A-D and upper perimeter groove 66. The first distance is indicated by reference numeral 78 in FIG. 4. Similarly, and also shown in FIG. 4, lower protrusions 76A-D and lower perimeter groove 67 are both located at a second distance from upper edge 61. The second distance is indicated by reference numeral 79. FIG. 3 illustrates the staggered nature of the protrusions around a perimeter of the inner surface of the sleeve. In particular, each upper protrusion 72A-D is spaced apart at ninety degree intervals around an inner perimeter of sleeve 60, the angle measured from a center of the sleeve. Similarly, each lower protrusion 76A-D is also spaced apart at ninety degree intervals around the inner perimeter, although out of phase by forty five degrees relative to the upper protrusions. A result of this arrangement is that a single protrusion is located at every forty five degree interval as measured from the center of the sleeve. In particular, and as shown in FIGS. 3 and 4, starting from upper protrusion 72A, a sequence of the protrusions in the clockwise direction is: lower protrusion 76B, upper protrusion 72B, lower protrusion 76C, and so on. The out of phase relationship between the lower protrusions and the upper protrusions is advantageous in that it is well suited for machining.

Turning to the particular shapes of the protrusions, as shown in FIGS. 4-6, lower protrusions 76A-D are distinguishable from upper protrusions 72A-D. Beginning with upper protrusions 72A-D, each upper protrusion is rectangular in shape and includes a planar elevated surface. Dimensions of the upper protrusions are approximately the same throughout their depth from the inner surface of the sleeve to the elevated surface. For upper protrusion 72A, elevated surface 73A is shown in FIG. 6. Lower protrusions 76A-D have rectangular dimensions immediately above inner surface 71, as shown in FIGS. 4 and 5, although each protrusion tapers in a direction away from the inner surface to a ridge that extends over a length of the protrusion. In this manner, each lower protrusion has a triangular profile when viewed in a circumferential direction parallel to lower edge 62. FIG. 5 illustrates lower protrusion 76A in particular, and ridge 75A that extends across its length.

Figure 7:
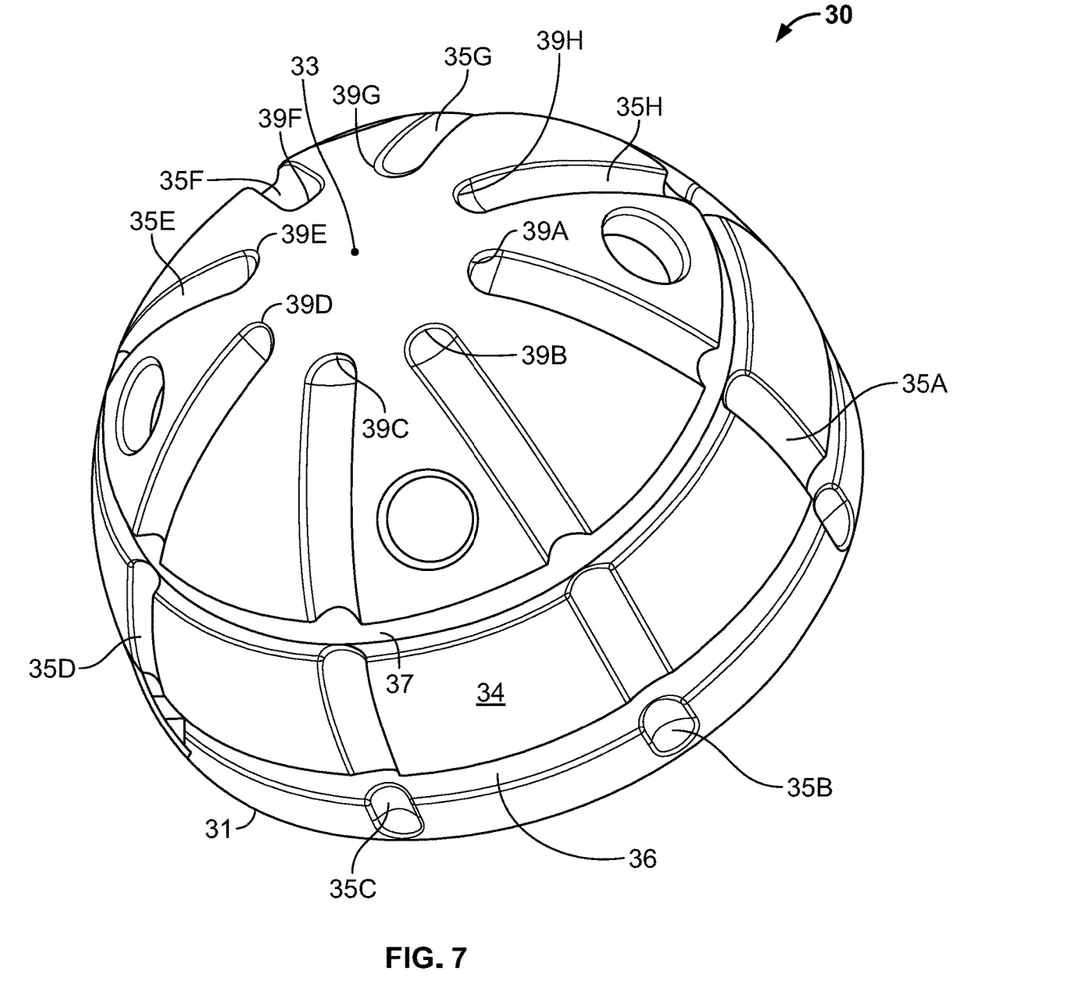
FIG. 7 is a perspective view of the liner of the assembly shown in FIG. 1.

Liner 30 is a hollow hemispherical structure as shown in FIG. 7. The liner is metallic, though it is contemplated that other materials may be used to form the liner. An outer surface 34 of liner 30 extends from an equatorial edge 31 to a pole 33. Equatorial edge 31 is also referred to herein as a rim. A region around pole 33 is also referred to herein as a polar region. In a pattern that corresponds to that of the grooves on the outer surface of sleeve 60, liner 30 includes a plurality of liner engagement features in the form of grooves thereon. Perimeter grooves recessed in outer surface 34 extend around a perimeter of liner 30 at different distances from, and parallel to, equatorial edge 31. Upper perimeter groove 36 is closest to equatorial edge 31 while lower perimeter groove 37 is further from equatorial edge 31 and closer to pole 33. Eight polar grooves 35A-H are recessed in outer surface 34 and extend in a direction orthogonal to the perimeter grooves as measured at an intersection between the two. In liner 30, each polar groove is equally spaced apart around a perimeter of the outer surface. Each polar groove 35A-H has a length from equatorial edge 31 that extends, in a direction orthogonal to equatorial edge 31, toward a pole 33 and ends at a respective location 39A-H corresponding to a first radius centered on pole 33. In this manner, a polar end of each polar groove is located at a distance from pole 33 at the first radius, measured between pole 33 and any one of locations 39A-H. It should be appreciated that the first radius may vary from that shown in FIG. 7, and in this manner, the polar end of each groove may be closer or further from the pole.

As with the grooves on sleeve 60, the perimeter grooves and the polar grooves of liner 30 form rounded troughs in outer surface 34 of liner 30 such that a width of each groove between its side edges is defined by a curved surface but the side edges themselves define an angle with respect to outer surface 34. Again, as with sleeve 60, the perimeter grooves are deeper than the polar grooves. The grooves on liner 30, similar to the grooves on sleeve 60, are shaped and located to enhance adhesion of the liner with cement.

Turning to the relationship between sleeve 60 and liner 30, sleeve 60 includes sleeve engagement features, e.g., protrusions, for mechanical fixation of the sleeve to the liner. FIGS. 2B-2D illustrate how sleeve 60 is mechanically fixed to liner 30. In sum, lower protrusions 76A-D are locked, and otherwise disposed, within lower perimeter groove 37, while upper protrusions 72A-D are similarly locked within upper perimeter groove 36. In this arrangement, the inner surface of the sleeve is flush with the convex outer surface of the liner. Disposal of the protrusions of the sleeve within grooves of the liner provides sufficient mechanical fixation to snap lock the elements to one another. In particular, upper protrusions 72A-D are intended to act as snap protrusions that lock into perimeter groove 36 of the liner and resist axial forces in both directions. Since groove 36 is semi-circular in cross-section and protrusions 72A-D are rectangular in shape, press-fit contact occurs between upper protrusions 72A-D and perimeter groove 36 on at least two points of contact when the sleeve is snap fit into place on the liner. Turning to lower protrusions 76A-D, each has a shape in the form of a right-angle triangle such that a base face of each lower protrusion 76A-D bottoms out on a corresponding groove face of the liner. This planar contact resists axial forces that act toward the lower end of the acetabulum during cement pressurization and curing, and supplements the snap lock of upper protrusions 72A-D. An illustration of the engagement between the sleeve and the liner is shown in FIGS. 2B-2D, where FIG. 2B illustrates upper protrusions 72A, 72C disposed within upper perimeter groove 36 and FIG. 2D illustrates lower protrusions 76B, 76D disposed in lower perimeter groove 37.

FIG. 2C illustrates a section view within the forty five degrees of separation between adjacent protrusions, and accordingly no protrusions that extend inward from the sleeve are visible. FIGS. 2B-2D also illustrate how grooves 65A-H, 66, 67 of sleeve 60 are generally aligned with grooves 35A-H, 36, 37, respectively, on liner 30. In this manner, when cement is used as an adhesive to secure liner 30 to an acetabular shell, the advantages of the grooves on the liner are not lost through the fixation of a sleeve to the liner, since the sleeve includes grooves on its outer surface aligned with those of the liner it covers. This is also shown in FIG. 1. The cement used for securement may be a bone cement. Although cement is referenced throughout the disclosure as an adhesive to secure the inner and outer acetabular constructs to one another, it should be appreciated that other similar technologies may also be used as known to those of skill in the art. In some examples of the assembled arrangement, the sleeve only covers the liner over an equatorial region of the liner. One advantage of assembly 10 is that sleeve 60 is snap locked to liner 30 without any additional elements or securement materials, such as adhesives.

The assembly or its constituent parts including the sleeve and the inner acetabular construct, e.g., liner, may be varied in many ways. In some examples, the sleeve may include an inner surface with protrusions all having the same shape. In other examples, the protrusions may be of three or more unique shapes. A particular shape of a protrusion may vary in any way desired. For instance, where a groove on the inner acetabular construct has a unique shape, the protrusion on the sleeve may have a shape customized for fixation to such a groove. In some examples, the protrusions may be out of phase by 22.5 degree angles as measured from a center of the sleeve or at any other angle. Similarly, one set of protrusions may be out of phase from another set of protrusions by any amount desired. Moreover, phase separation between adjacent protrusions may vary from one pair of protrusions to the next around the perimeter of the sleeve. Further, a quantity of protrusions on the inner surface of the sleeve may be any amount deemed advantageous or practical, and may exceed the eight protrusions on the sleeve of the depicted embodiment. In some instances, the protrusions may be positioned at three or more separate levels on the sleeve, each level defined by a particular distance from an edge of the sleeve. In any of the above examples, a shape of the protrusions in any particular level or location on the sleeve may be unique or may be part of a pattern of protrusions of that shape.

In further examples, the perimeter and/or polar grooves on an outer surface of the sleeve may be greater or fewer in number. A spacing between the grooves may be any desired amount, and may be a single spacing around the perimeter of the sleeve, or may vary from one groove to an adjacent groove. In other examples, the polar grooves may have an equatorial end spaced from the upper edge. In some examples, the polar grooves are deeper relative to the outer surface of the sleeve than the perimeter grooves. In still other examples, any individual groove or group of grooves may have a depth different from other grooves of the sleeve. In still further examples, an orientation of any one groove or group of grooves may be slanted so that a perimeter groove has a length at an angle relative to the upper edge of the sleeve or a polar groove is not orthogonal to the upper edge. A shape of one or more grooves on the sleeve may vary in any number of ways. The trough that defines each groove may be v-shaped or square shaped, for example. In still further examples, the sleeve may have a size that corresponds to a greater or lesser portion of the outer surface of the inner acetabular construct than that of the sleeve of FIG. 1. In any of the above examples, the sleeve may have a lower edge with cut outs or a lower edge that is angled relative to the upper edge over a portion of its length. In some examples, the porosity of the sleeve material is sufficient to promote interdigitation with cement.

In some examples, the liner engagement features on the inner acetabular construct, whether grooves or otherwise, may be varied in any number of ways already described for the grooves of the sleeve. Additionally, the inner acetabular construct may include any number of cement spacers located in any pattern or random placement. In some examples, the polar grooves may extend toward the pole of the inner acetabular construct in a manner such that ends of the polar grooves are immediately adjacent one another. In some examples, the polar grooves may vary in length relative to one another. The inner acetabular construct may have one or more perimeter grooves spaced apart from one another in any amount desired.

In some examples of the assembly, the inner acetabular construct may include protrusions while the sleeve includes an inner surface with grooves or other recesses to provide a snap lock connection between the elements. It is also contemplated that the engagement features on the sleeve and/or the liner, such as the grooves and protrusions on the sleeve and the grooves on the liner, may be varied in any number of ways described in U.S. Pat. No. 6,758,864 and in U.S. Pat. App. Pub. No. 2015/0025647, the disclosures of which are hereby incorporated by reference herein in their entirety.

Figure 11:
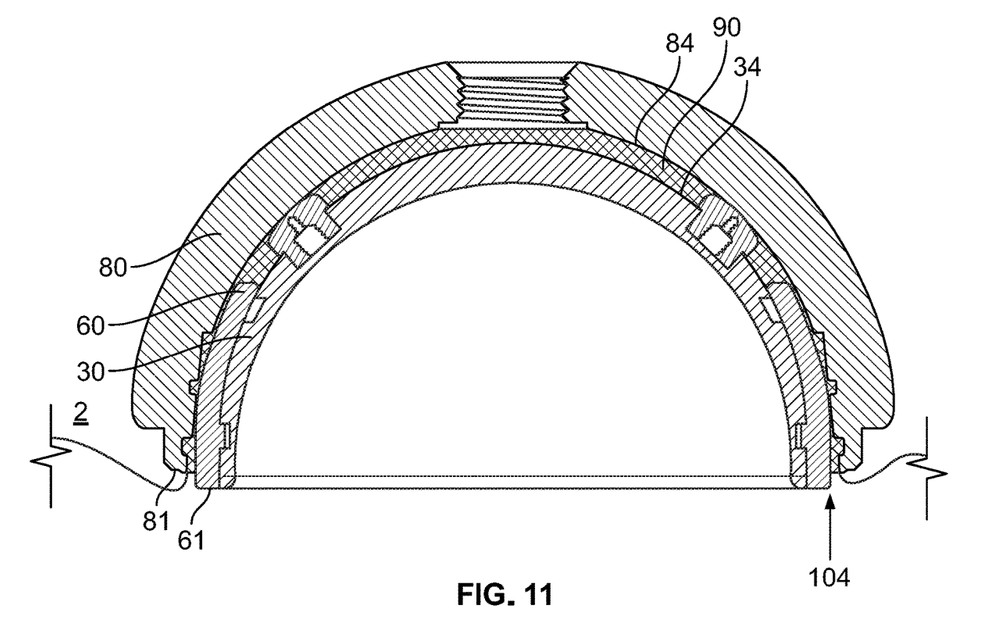

In another aspect, the present disclosure relates to systems for hip replacement. In one embodiment, a system includes assembly 10, an outer acetabular construct in the form of an acetabular shell, also referred to herein as an acetabular cup, and cement. The acetabular shell is sized and includes features for direct engagement to a bone surface of a mammalian acetabulum. The cement secures the assembly to the acetabular shell. In particular, the assembly is disposed within the shell, with a gap between the outer surface of the assembly and the acetabular shell filled by the cement. One example of this system is illustrated in FIG. 11, where the acetabular shell is denoted by reference numeral 80. In some embodiments, the outer acetabular construct may be a structure other than an acetabular shell. In other embodiments, a system includes any assembly contemplated in the present disclosure secured to an outer acetabular construct with cement. It should be appreciated that a shape of the outer acetabular construct and its features may vary in accordance with the particular features of the inner acetabular construct of the assembly.

In another aspect, the hip implant components contemplated herein may be included together as part of a kit. In one embodiment, a kit includes two assemblies each with a sleeve and an inner acetabular construct, where each assembly has a unique size. In another embodiment, a kit includes two assemblies, where each assembly has a unique shape. In another embodiment, a kit includes a group of assemblies that are all the same. In yet another embodiment, a kit includes a first set of assemblies that are all the same along with a second set of assemblies different from the first set. It should be appreciated that the above embodiments are illustrative and that any combination of the above embodiments may be used to form a kit.

In some embodiments, a kit includes an assembly and an outer acetabular construct, such as an acetabular shell. Any number and variety of outer acetabular constructs may be included with an assembly in a kit, and any combination of assemblies such as those described in the embodiments above may be included in a kit with one or more outer acetabular constructs. In these embodiments, a quantity of cement may also be added to the kit. In other embodiments, accessories for an acetabular implant such as implantation or removal tools, or additional components that are implanted along with the acetabular constructs may also be included.

The kit may be varied in many ways. For example, the various combinations of elements of any contemplated kit may be included in a single package or distributed among multiple packages. In other examples, the kit contemplated herein may be accompanied by an instruction manual on how to perform one or more of the methods of using the contents of the kit.

Figure 8:
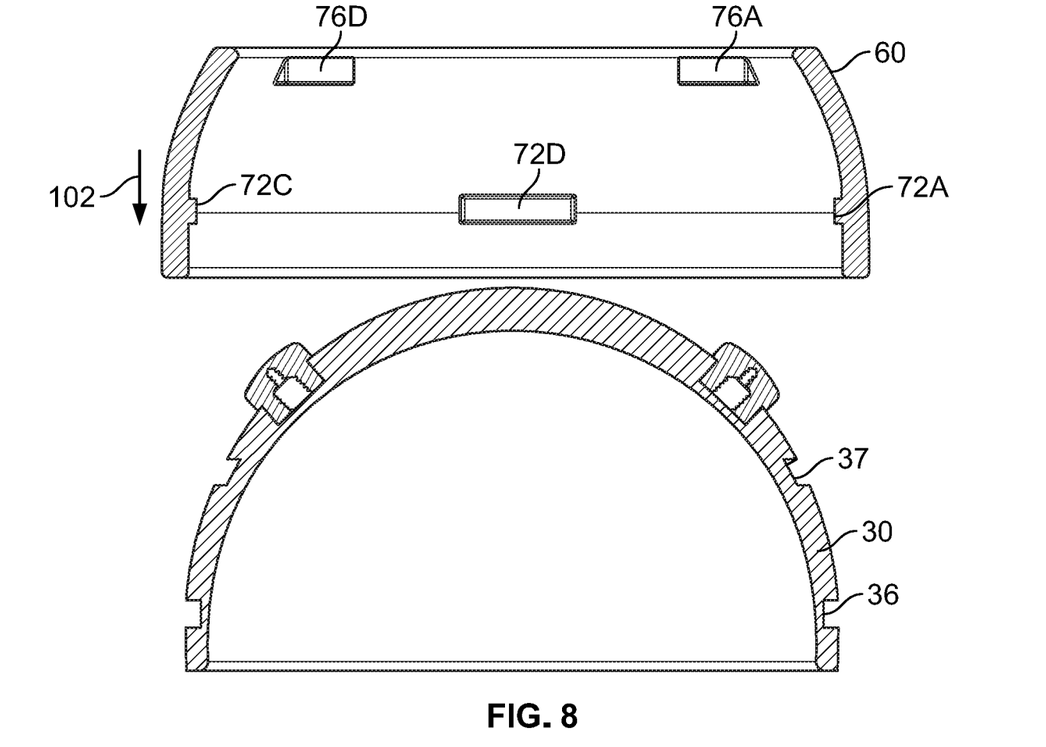
FIGS. 8-11 are cross-sectional views of steps of a method of assembling the sleeve and the liner according to one embodiment of the disclosure.
Figure 9:
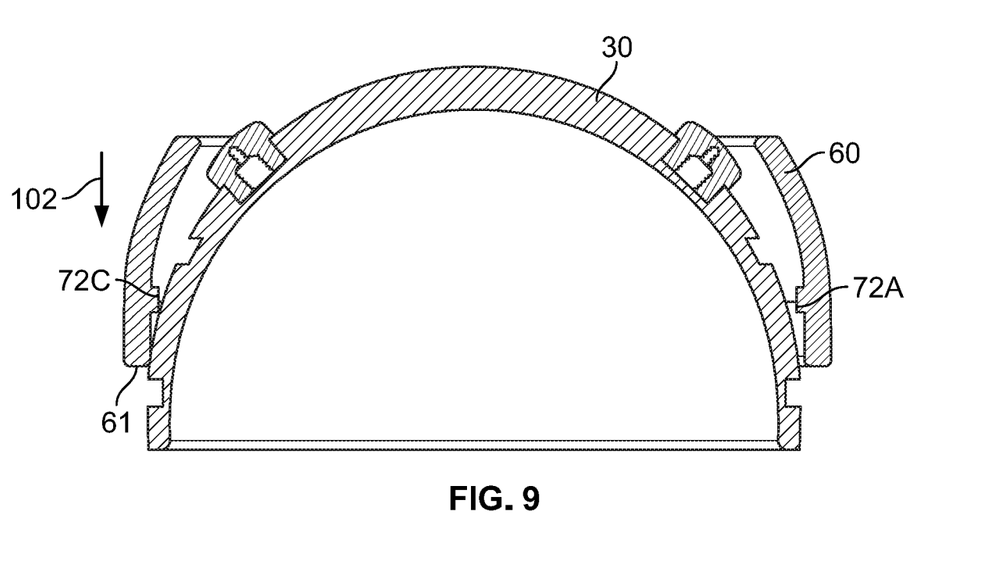
Figure 10:
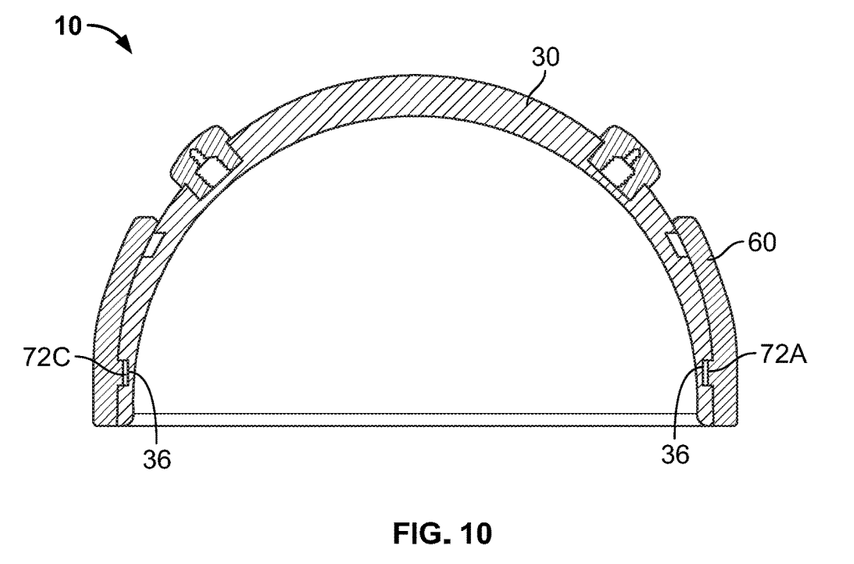

In yet another aspect, the present disclosure relates to a method of assembling a sleeve and an inner acetabular construct to form an assembly and/or fitting the assembly into an acetabular shell. In one embodiment, with reference to FIGS. 8-11, sleeve 60 and liner 30 are introduced to form assembly 10. Initially, as shown in FIG. 8, sleeve 60 is positioned over pole 33 of liner 30. Then, as shown in FIG. 9, sleeve 60 is slid and otherwise pressed over liner 30 so that inner surface 71 of sleeve 60 becomes closer to outer surface 34 of liner 30 as the sleeve is advanced toward an equatorial region of the liner. Reference numeral 102 indicates a direction of sleeve advancement. When lower protrusions and upper protrusions on sleeve 60 become aligned with corresponding perimeter grooves on liner 30, sleeve 60 snaps into place over liner 30 and, with sufficient mechanical fixation between the two, the sleeve becomes locked to the liner. FIG. 10 illustrates the sleeve locked to the liner. In particular, upper protrusions, including protrusions 72A, 72C shown in FIG. 10, are disposed within upper perimeter groove 36. Also, though not visible at the cross-section shown in FIG. 10, the lower protrusions are disposed in lower perimeter groove 37. The geometry of the protrusions and their alignment with the grooves of the liner lock the sleeve into place over the liner. More specifically, each protrusion is locked within a groove of the liner. When combined as shown in FIG. 10, sleeve 60 and liner 30 together define assembly 10.

One reason the protrusions on the sleeve are advantageous is that they provide constraint against movement and thereby lock the sleeve in place relative to the liner. In particular, upper protrusions, when locked into place within the upper perimeter groove of the liner, axially and rotationally constrain the sleeve relative to the liner. The lower protrusions, when locked into place within the lower perimeter groove of the liner, restrain movement of the sleeve relative to the liner in the axial direction. Put another way, the lower protrusions keep the sleeve from withdrawing from the liner once locked into place. The axial constraint provided by the lower protrusions is sufficient so that even under pressure from cement curing between the assembly and an acetabular shell, the sleeve is restrained from slipping off the liner or otherwise becoming detached.

With the sleeve and the liner locked together, assembly 10 is ready to be fit into an acetabular shell 80 positioned within an acetabulum (within surrounding bone 2) of a mammalian patient. It should be appreciated that acetabular shell 80 may be newly fixed to the acetabulum as part of a new hip replacement surgery without any existing components, or it may be a preexisting acetabular shell left in place in the patient after a previously implanted inner acetabular construct and/or bearing(s) has been removed. Moreover, instead of an acetabular shell, the existing construct may be a cage or another outer acetabular construct. It should also be appreciated that the process of attaching an outer acetabular construct to a bone may vary as a function of the implant system utilized.

Prior to placement of the assembly 10 into acetabular shell 80, the shell is prepared for application of cement. Then, cement 90 is applied and distributed over an inner surface 84 of shell 80. Once the application of cement 90 is deemed adequate, then assembly 10 is advanced into an opening of acetabular shell 80, as shown in FIG. 11. A direction of the advancement is indicated by reference numeral 104. During this step, the assembly may be placed under pressure to ensure a proper fit of assembly 10 within acetabular shell 80. A fit may be considered proper when equatorial edge 31 of liner is parallel to an upper edge 81 of acetabular shell 80. When assembly 10 is properly positioned, as shown in FIG. 11, sleeve 60 is located in between outer surface 34 of liner 30 and inner surface 84 of shell 80. As a result, a space that would otherwise be occupied by cement 90 in an implanted condition is instead occupied by sleeve 60. Nonetheless, assembly 10 is positioned and sized such that sufficient space exists between the outer surface of the sleeve and the inner surface of the acetabular shell in the equatorial region so that cement therebetween is sufficient for fixation of the respective elements. In this manner, cement is distributed within a space between the liner and the acetabular shell in at least a portion of the equatorial region and a portion of the polar region. In some examples, cement is disposed throughout an entirety of the space between the liner, or sleeve over it, and the acetabular shell, including an entirety of the equatorial and polar regions. In some examples, the sleeve may include one or more openings. In such examples, the liner with sleeve attached may be positioned in the acetabular shell at any stage in the preparation of an inner surface of the acetabular shell.

In examples where the acetabular constructs are metallic, the assembly, when cemented inside a metallic acetabular shell, prevents equatorial regions of the metallic liner from being directly integrated to the metallic acetabular shell by cement due to the presence of the polymeric sleeve in between. This arrangement renders it easier to remove the liner from the shell during a revision procedure.

In another embodiment, a method only involves the steps of bringing together sleeve 60 and liner 30 to form assembly 10. In yet another embodiment, a method begins with assembly 10 already assembled. Initially, an acetabular shell is prepared through placement of cement thereon, then assembly 10 is fit into the acetabular shell in a desired manner to obtain alignment between the liner and the shell, such as is shown in FIG. 11. In other embodiments, a method may include any number of the steps of assembling a sleeve and an inner acetabular construct and/or placing the assembly in an outer acetabular construct, and may further include steps for securement of the outer acetabular construct into an acetabulum. The steps taken to prepare the acetabulum and to secure the outer acetabular construct to the acetabulum may be those known to persons of ordinary skill in the art.

In any one of the above embodiments, any embodiment or variant of the sleeve and the inner acetabular construct, including liners, contemplated by this disclosure may be used to perform a method of assembling the sleeve and inner acetabular construct to form the assembly and/or fit the assembly into an acetabular shell. In other embodiments, the liner may be used without the sleeve when implanted directly into bone, the grooves throughout the liner surface providing enhanced engagement with cement disposed in between the liner and the bone.

Figure 12:
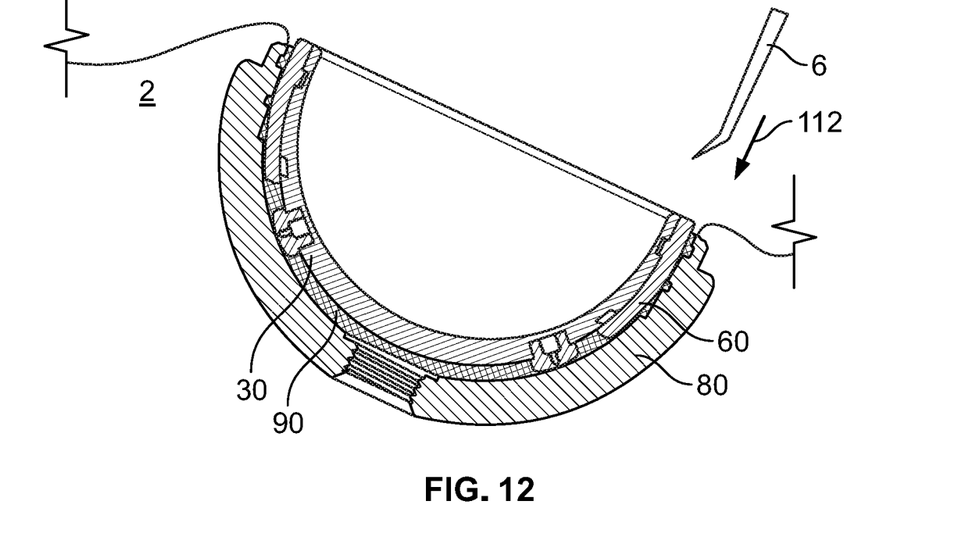
FIGS. 12-14 illustrate steps in a method of removing a liner from an acetabular shell located in an acetabulum of a patient according to one embodiment of the disclosure.

In yet another aspect, the present disclosure relates to a method of removing a liner of an acetabular implant system without removing an outer acetabular construct, such as an acetabular shell. In one embodiment, shown in FIGS. 12 through 14, a tool 6 is brought to the surgical site and placed in between liner 30 and sleeve 60 of assembly 10. In some alternative approaches, it may also be possible to place the tool between the acetabular shell and the sleeve. Tool 6 may be any conventional tool used in revision procedures in the hip or other joints, such as an osteotome, chisel or curette. Once tool 6 is wedged in between liner 30 and sleeve 60, sleeve 60 is removed from its locked position on the liner by pulling protrusions 72A-D, 76A-D out from within grooves 36, 37, respectively. During this step, removal of the sleeve may be facilitated through cutting, deforming, chipping and/or other conventional techniques to hasten and otherwise simplify the removal of the sleeve. In some examples, when sufficient cement material is removed, the tool may be used to pry out the sleeve from below or from any location where grip is obtained. Because the sleeve is a polymer or other similar material, a surgeon has greater flexibility regarding techniques that may be employed to remove the sleeve from the liner. For example, the sleeve may be cut, bent or otherwise manipulated to aid in the process of removal. During this process, cement immediately in between the sleeve and the acetabular shell may be removed in part or in its entirety, as deemed necessary or otherwise advantageous under the circumstances. In some examples where a sleeve is removed from the liner, no more than 60% of an outer surface area of the liner is covered by cement that remains engaged the acetabular shell after removal. In other examples, 35% to 45% of the outer surface area of the liner remains engaged to the acetabular shell by cement after removal. In still further examples, less than 40% of the polar grooves and none of the perimeter grooves are covered by cement that engages the liner to the acetabular shell after removal of the sleeve.

Figure 13:
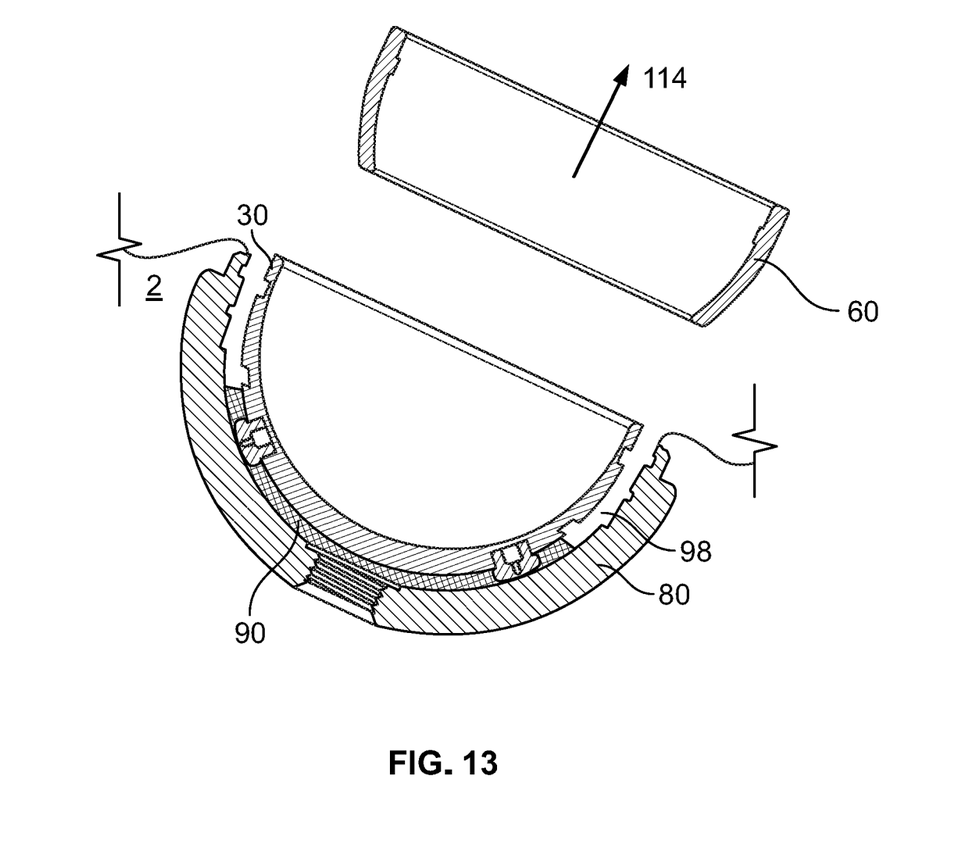

FIG. 13 illustrates the liner and the acetabular shell within the body once the sleeve is removed, as indicated by reference numeral 114. With sleeve 60 removed, a void 98 is left between liner 30 and shell 80 in the equatorial region where the sleeve was previously disposed. In this manner, at least part of the equatorial region is not bound together by cement 90, which only binds liner 30 with acetabular shell 80 in a polar region, located approximately over a portion of liner 30 bound to shell 80 by cement 90 as shown in FIG. 13. Because of this void 98, access to deeper regions of the liner is made possible. Tool 6 or another tool is used at this juncture to move, rock and/or rotate liner 30 relative to acetabular shell 80 to weaken the cement based securement of the liner to the shell. For example, an osteotome may be used to lever out the liner. Because only a small portion of the shell and the liner are engaged by cement, the cement interface between the two is weakened significantly compared to a cement interface spanning an entire hemisphere of the respective acetabular constructs, thereby lessening the force required to remove the liner from the shell to a significant degree. Also, because of the significant depth accessible between the liner and the shell within void 98, the tool may be used with increased leverage to lever out the liner when compared to a fully cemented pair of acetabular constructs.

Figure 14:
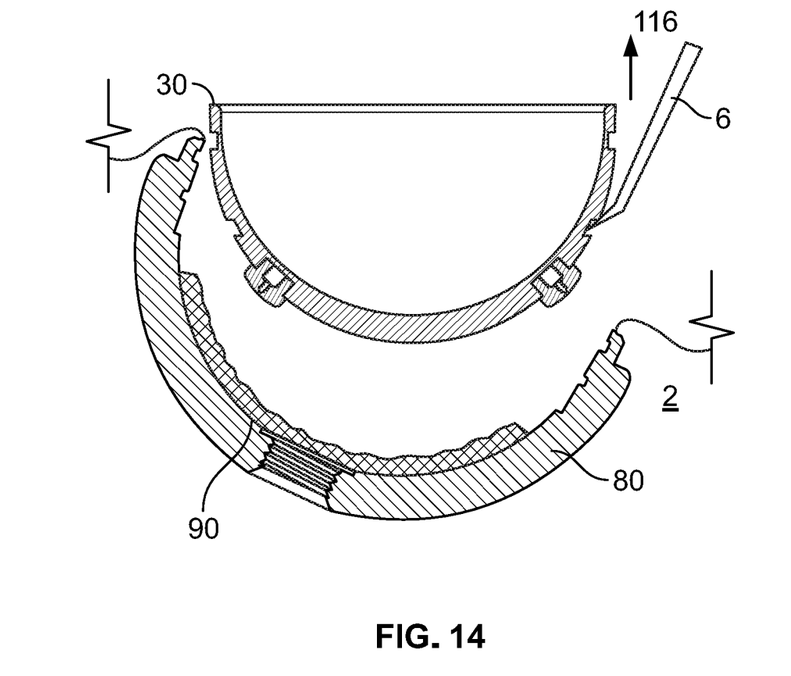

As shown in FIG. 14, because cement only binds the liner and the acetabular shell over part of their respective surface areas facing one another once the sleeve is removed, the liner is removed with relative ease using simple tools in a manner indicated by reference numeral 116. Moreover, because forces required to remove liner 30 from acetabular shell 80 are low relative to a fully cemented interface between acetabular constructs, this technique allows liner 30 to be removed without pulling acetabular shell 80 from the acetabulum. In this manner, the acetabular shell 80 remains intact and secured to bone 2, and the acetabular shell is not damaged in the process of removal of the liner. Additionally, this method also significantly reduces the risk of removing or damaging bone structures in and around the acetabulum. Through the above method, the liner may be removed predictably in a relatively short period of time. Once the liner removal process is complete, a new liner may be implanted and locked while leaving an existing acetabular shell in place.

The devices and methods of the disclosure are particularly well adapted for acetabular constructs that form a modular dual mobility system, but may also be employed in other circumstances where two metal constructs are intended to be cemented to one another. In some examples, the assembly can be used with dual mobility bearings placed inside of the inner construct and an outer surface of the inner construct cemented to the outer construct with cement spacers placed at predetermined, spaced locations on the outer surface of the inner construct.

The assembly is advantageous for use in methods of securing an inner construct, e.g., acetabular liner, to an outer construct, e.g., acetabular shell, where both the inner and outer constructs are metallic. It is advantageous in that it is easily revisable, modular and may be employed in dual mobility hip implant systems, either as a new implant or as a replacement. Another advantage of the assembly is that grooves on outer surfaces of the sleeve and the liner are exposed for receipt of cement to engage the assembly to the outer construct. In an alternative arrangement, the inner construct may be cemented to the outer construct or to a bone without the sleeve. The inner construct may be provided without the sleeve, or the sleeve may be unlocked from the inner construct to prepare for such use. This configuration may be desirable when the inner construct is intended for cementing directly onto a bone surface.

Yet another advantage is the matching geometry of the grooves on the sleeve and the inner construct. In particular, when the sleeve is mechanically fixed to the inner construct to lock the respective elements, the grooves of the sleeve are aligned with the grooves on the inner construct that are covered by the sleeve. Thus, although some portions of the grooves on the inner construct are covered by the sleeve, those portions exist on the sleeve at approximately the same radial location as extant on the liner. Thus, the assembly, when cemented to an outer acetabular construct, produces similar cement coverage and cement fixation as that obtainable when the inner construct is cemented by itself directly to an outer construct or to bone.

Although the disclosure herein has been described with reference to particular embodiments, it is to be understood that these embodiments are merely illustrative of the principles and applications of the present disclosure. It is therefore to be understood that numerous modifications may be made to the illustrative embodiments and that other arrangements may be devised without departing from the spirit and scope of the present disclosure as defined by the appended claims.

The invention claimed is:

1. An acetabular implant system comprising:
a liner including a convex outer surface shaped to correspond to an interior of an acetabular cup and having an equatorial region and a polar region, the convex outer surface including a plurality of liner engagement features thereon; and
a sleeve including an inner surface and an outer surface, the inner surface having a plurality of sleeve engagement features thereon and the inner surface sized to be flush with the convex outer surface of the liner,
wherein when the sleeve is engaged with the liner, the liner engagement features engage the sleeve engagement features, and
wherein when the sleeve is engaged with the liner, the outer surface of the sleeve stands proud of the convex outer surface of the liner and a distance from the outer surface of the sleeve to the liner is approximately the same at an upper edge of the sleeve and at a lower edge of the sleeve.

2. The acetabular implant system of claim 1, wherein when the sleeve is engaged with the liner, the sleeve covers a first portion of the polar region of the convex outer surface of the liner without covering a second portion of the polar region.

3. The acetabular implant system of claim 1, wherein the plurality of liner engagement features include a circumferentially extending recess parallel to a rim of the liner.

4. The acetabular implant system of claim 3, wherein the plurality of sleeve engagement features are protrusions shaped to fit within the circumferentially extending recess on the convex outer surface of the liner.

5. The acetabular implant system of claim 4, wherein the plurality of liner engagement features include a second circumferentially extending recess parallel to the rim of the liner and wherein the protrusions on the inner surface of the sleeve include a first protrusion at a first distance from a rim of the sleeve and a second protrusion at a second distance from the rim of the sleeve, the first protrusion fitting within the circumferentially extending recess and the second protrusion fitting within the second circumferentially extending recess.

6. The acetabular implant system of claim 1, wherein the sleeve includes an outer surface with a second plurality of sleeve engagement features thereon.

7. The acetabular implant system of claim 6, wherein the plurality of liner engagement features include a plurality of recesses extending from a location proximal to a pole of the liner to a rim of the liner and the second plurality of sleeve engagement features include a plurality of recesses aligned with the plurality of recesses on the convex outer surface of the liner when the sleeve is engaged with the liner.

8. The acetabular implant system of claim 1, wherein the plurality of liner engagement features are one of recesses and protrusions and the plurality of sleeve engagement features are the other of recesses and protrusions.

9. The acetabular implant system of claim 1, wherein the sleeve is a polymer material and the liner is a metallic material.

10. The acetabular implant system of claim 1, further comprising the acetabular cup.

11. An acetabular implant comprising:
  an acetabular cup adapted to seat within an acetabulum of a mammal;
  a liner disposed in the acetabular cup; and
  a sleeve with an inner surface engaged to a portion of an outer surface of the liner such that the sleeve is disposed in between the acetabular cup and the liner, a portion of the inner surface of the sleeve being concave in a plane passing through an apex the liner, the plane bifurcating the liner,
  wherein the liner with the sleeve engaged thereto is cemented to the acetabular cup.

12. The acetabular implant of claim 11, wherein the sleeve is a segment of a hollow sphere between two parallel planes and one of the two parallel planes bisects the hollow sphere.

13. The acetabular implant of claim 11, wherein the liner includes an equatorial region and a polar region, the sleeve separating the liner from the acetabular cup solely in the equatorial region.

14. The acetabular implant of claim 13, wherein the cement for engagement of the liner with the acetabular cup is disposed between the liner and the acetabular cup over an entirety of both the equatorial region and the polar region of the liner.

15. The acetabular implant of claim 11, wherein the sleeve includes an inner surface with protrusions thereon, the protrusions being engaged to corresponding recesses on an outer surface of the liner.

16. A method of removing a liner from an acetabular cup secured to an acetabulum comprising:
  ensuring that the acetabular cup with the liner cemented therein is accessible to an extent sufficient to remove the liner;
  causing a sleeve engaged to an outer surface of the liner to become disengaged from the liner;
  removing the sleeve such that the liner remains at least partially cemented to the acetabular cup in a polar region of the liner; and
  after removing the sleeve, removing the liner from the acetabular cup such that the acetabular cup remains secured to the acetabulum.

17. The method of claim 16, wherein removing the sleeve further comprises removing a portion of the cement immediately in between the sleeve and the acetabular cup.

18. The method of claim 17, wherein removing the sleeve leaves no more than 60% of an outer surface of the liner covered by cement that secures the liner to the acetabular cup.

19. The method of claim 16, wherein causing the sleeve to become disengaged from the liner further comprises prying a tab on an inside surface of the sleeve from a groove on an outside surface of the liner.

20. The method of claim 16, wherein removing the liner involves rotating the liner relative to the acetabular cup.

* * * * *